United States Patent [19]

Freitag et al.

[11] Patent Number: 5,132,208
[45] Date of Patent: Jul. 21, 1992

[54] TEST CARRIER FOR THE ANALYSIS OF A SAMPLE LIQUID

[75] Inventors: Helmut Freitag, Indianapolis, Ind.; Hans-Erich Wilk, Lorsch, Fed. Rep. of Germany; Anselm Rothe, Birkenau, Fed. Rep. of Germany; Heino Eikmeier, Lorsch, Fed. Rep. of Germany

[73] Assignee: Boehringer Mannheim GmbH, Mannheim, Fed. Rep. of Germany

[21] Appl. No.: 189,782

[22] Filed: May 3, 1988

[30] Foreign Application Priority Data

May 9, 1987 [DE] Fed. Rep. of Germany ....... 3715485

[51] Int. Cl.[5] ................................................ C12Q 1/54
[52] U.S. Cl. ...................................... 435/7.1; 422/56; 422/57; 422/60; 435/4; 435/14; 435/7.9
[58] Field of Search ............... 435/14, 7, 810; 422/56, 422/57

[56] References Cited

U.S. PATENT DOCUMENTS 4,312,834 1/1982 Vogel et al. .................... 436/71

OTHER PUBLICATIONS

Chemical Abstracts General Subject Index 11th Collect. vol. 96-105 (1982-1986) p. 4602GS.

*Primary Examiner*—Sam Rosen
*Attorney, Agent, or Firm*—Felfe & Lynch

[57] ABSTRACT

The present invention provides a test carrier for the analysis of a sample liquid and especially of a body fluid, having a porous test layer (8, 13) which contains a solid component (9, 17), wherein the solid component (9, 17) is coated with a protein which is insoluble in the sample liquid under the test conditions. A process for the production of this test layer is also disclosed, wherein the protein is dissolved in a solvent under conditions under which the solubility of the protein is sufficiently high in order to dissolve a certain minimum amount of the protein, the solid component of the test layer is contracted with the solution and the solubility is reduced to such an extent that the component is coated by the precipitating protein.

19 Claims, 1 Drawing Sheet

TEST CARRIER FOR THE ANALYSIS OF A SAMPLE LIQUID

FIELD OF THE INVENTION

The present invention is concerned with a test carrier for the analysis of a sample liquid with a porous test layer which contains a solid component, as well as with a process for the production of such a test carrier.

BACKGROUND OF THE INVENTION

For the qualitative or quantitative analytical determination of sample liquids, especially of body fluids, such as blood or urine, in recent times so-called carrier-bound tests have been increasingly used. In these test devices, reagents are embedded in at least one test layer which is brought into contact with the sample. The reaction of sample and reagents gives rise to a detectable signal and especially to a colour change. This can be visually evaluated in simple cases. In the case of quantitative determinations, the evaluation preponderantly takes place with the help of an apparatus and especially reflection photometrically.

Test carriers are frequently made as test strips having a longitudinal support layer of a synthetic resin material to which are supplied one or more test layers. However, other forms of test carriers are known, for example, in the form of quadratic or rectangular platelets.

Test carriers and the associated evaluation devices, which together are referred to as test carrier analysis systems are, in comparison with the previously known wet chemical analysis processes, simple to handle and the apparatus are inexpensive. Consequently, ever more demanding analyses are, to an increasing extent, carried out with the help of test carriers. This has resulted in the development of test carriers which contain several test layers. The test layers are so arranged on a test carrier on top of one another or next to one another that a desired course of the test takes place. By means of appropriate constructional measures, it is even possible to achieve a multi-stage course of a reaction (see Federal Republic of Germany Patent Specification No. 36 38 654).

In particular, the test layers fulfill two functions:

a) Reagent carrier function: Dry reagents are contained in the layer in elutable or carrier-fixed form. Elutable reagents thereby are dissolved or dispersed by the sample liquid and mostly first react after elution into the liquid phase, whereas carrier-fixed reagents participate in the reaction in fixed form.

b) Liquid transport function: The test layers serve for the transport of the sample liquid within the test carrier.

The test layers mostly fulfil both functions simultaneously but sometimes there are used solely liquid transport layers (which do not contain reagents) or solely reagent layers (which do not bring about a liquid transport).

The present invention is especially concerned with porous test carrier layers. For the reagent carrier function, the porosity is usually advantageous because of the large surface area involved therewith. At the same time, in general, porous layers fulfill a liquid transport function which is based upon the capillary forces acting in the layer.

Porous test layers have at least one solid component which, alone or with other components, forms a three-dimensional, open-pored structure. The structure can be very different. Thus, for example, test layer papers or porous synthetic resin structures are known which can also be referred to as open-pored membranes or porous films.

Of especial importance for the present invention are textile structures, for example, fabrics or fleece in which the solid component is formed from filaments or threads which are intertwined with one another. Of course, several different materials can thereby also be used which form different solid components.

A further important feature of the present invention are particle-composite structures. Particles, for example, synthetic resin spheroids or inorganic particles thereby form a first solid component. The particles are connected together with an appropriate adhesive, frequently a polymer, to give a three-dimensional open-pored structure. The particles which form the first solid component are collectively referred to as opener particles. Several Different particle materials can be used which form different solid components of the test layer.

The term "solid component" is to be broadly understood to mean that every solid component of a test layer is included, regardless of whether it is itself participating in the structural composition of the test layer or whether it is merely integrated therein as is, for example, the case with the often used particles of titanium dioxide in test layers for reasons of optical reflection.

Very high requirements are demanded of test layers for modern quantitative test carriers. This applies, in particular, to immunochemical processes.

The biochemical reagents necessary for such processes, especially enzymes or enzyme conjugates, must be available for the reaction in the course of the test in very exactly pre-determined amounts. This is in contradistinction to most well-known clinical-chemical processes in which such reagents are usually used in excess without this having a substantial influence on the accuracy of the result. Consequently, immunochemical processes can, as a rule, only be carried out on solid carriers if the necessary biochemical reagents can be applied to a test carrier in a precisely measured amount, if there is no decrease of their enzyme activity even after comparatively long storage and if there is an unchanged dissolving behaviour during the storage up to the time of use.

Test layers for immunochemical tests are also subject to special requirements with regard to the transport properties. Here, it is, in particular, a question of the course of reactions in which the test layer contains an immunological binding component, for example an antibody, in carrier-fixed form and, in the course of a test, a liquid flows therethrough which contains a binding component complementary thereto, for example an antigen. The accuracy of such determinations is, on the one hand, substantially dependent upon the fact that the antigen transported through the test layer binds completely with the carrier-fixed antibody. In addition, however, it is also important that, as far as possible, no non-specific binding takes place. Thus, for example, antigen-antibody complexes formed in a preceding reaction step are to pass as unhindered as possible through the test layer functioning as separation layer, as is explained hereinafter in more detail. In general, in the case of various test processes, it is to be prevented that macromolecular organic test components contained in a liquid flowing through a test layer enter into an undesired binding with any of the solid components of the test layer.

SUMMARY OF THE INVENTION

These difficult requirements are not fulfilled to a sufficient extent by the known test layers. Therefore, it is an object of the present invention to provide test layers for test carriers which have improved properties with regard to the reagent carrier function and/or with regard to the transport function.

Thus, according to the present invention, there is provided a test carrier for the analysis of a liquid sample, especially of a body fluid, with a porous test layer which contains a solid component, wherein the solid component is coated with a protein which is insoluble in the sample liquid under the test conditions.

This means that under the conditions under which the analysis takes place on the test carrier, the protein must be insoluble to such an extent that the coating of the solid component remains intact. Conventional analytical determinations on test carriers take place at pH values of from about 5.5 to 8 and at temperatures of from 20 to 37° C. Casein has proved to be very advantageous for the present invention since, under these conditions, it is almost completely insoluble. Edestin is another protein which can advantageously be used. However, the possibilities of using it are limited due to its black colour. The suitability of other proteins which are insoluble under the particular test conditions can readily be ascertained by the person skilled in the art.

In order to coat the solid component with the protein, this is treated with a solution of the protein. The solution is prepared under conditions under which the solubility of the protein is sufficiently high in order to dissolve the minimum amount necessary for the coating. Thereafter, the solid components are contacted with the solution and the solubility of the protein is reduced to such as extent by appropriate means that at least a part of the protein precipitates out and the component is coated with the precipitated protein. Details of the process depend upon the particular individual case.

Thus, for example, the necessary solubility for the preparation of the treatment solution can be achieved by the choice of an appropriate solvent, in which case, after contacting with the solid component, a precipitating agent is added to the solution in order to initiate the coating.

It is also possible to proceed in such a manner that a highly diluted solution of the protein is used and the solvent is then evaporated in order to initiate precipitation of the protein. Of course, the solubility can also be influenced in the desired manner by changing the temperature.

Especially preferably, the solubility is changed by an appropriate change of the pH value, for example by the addition of sodium hydroxide. Thus, for example, it has been shown that casein at a pH value of at least 10.5 is so substantially soluble in water that a sufficient protein concentration can be achieved. In this case, the precipitating out of the protein is achieved by a rebuffering to a pH value of from 5.5 to 8. This results in a high quality coating of the solid component.

The solid component can be contacted with the protein solution in various ways. It is preferable to coat the whole of the test layer, i.e. not only one or more solid components thereof. This applies especially to test layers with a textile structure, for example in the case of fleece or fabrics. The contacting can here take place by spraying or in the immersion impregnation processes which are common in test carrier production.

Insofar as only individual components of a test layer are to be coated with the insoluble protein, this must take place before they are integrated into the test layer. This is of particular importance in the case of the above-mentioned particle-composite structures, in which case the particles are mixed into the protein solution, whereafter the coating is carried out by precipitating out the protein. Finally, the coated particles are separated off by sieving or centrifuging. The so-coated particles are integrated into the test layer. Especially preferably, this takes place in such a manner that the particles are mixed with a film former, the mixture is coated on to a substrate and allowed to harden out to give a porous test layer which contains the particles. In this regard, reference is made to U.S. Pat No. 4,312,834.

The protein coating does not have to completely cover the surface of the solid component. On the contrary, depending upon the microstructure of the material of which the solid components consists, it is to be reckoned that, in general, a small part of the solid surface remains uncovered. However, this has not proved to be disadvantageous.

In order to achieve a sufficient covering of the surface, a sufficient minimum amount of protein, referred to the amount of the solid component to the coated, is necessary. In individual cases, this can be determined experimentally. We have found that exceeding this amount is, as a rule, not critical. An excess does not result preponderantly in a thickening of the coating but rather it precipitates out freely and can, therefore, readily be separated off.

The concentration of the protein in the coating solution can vary within wide limits. However, concentrations of from 0.1 to 1% have proved to be practical.

The protein coating according to the present invention has proved to be especially advantageous when the test layer contains a biochemical reagent in elutable form. The reagent can be, in particular, an enzyme or an enzyme conjugate, for example, with an antibody or antigen. Especially for reagent layers which contain the enzyme galactosidase, which is frequently used as labelling enzyme for immune tests, the present invention has proved to be practical. It is achieved that a definite amount of reagent incorporated into the test layer in the production of the test carrier, even after storage for several years, can be eluted with very good precision and is thus available for the reaction. In this connection, test layers with a textile structure, especially fabrics or fleece, made of polyester or polyamide are particularly preferred.

$\beta$-galactosidase is to be understood to be the enzyme E.C. 3.2.1.23. $\beta$-galactosidase conjugates are to be understood to be compounds of galactosidase with antibodies (IgG as well as Fab), haptens, proteins and the like. The preparation of such conjugates which are, in principle, known takes place according to the techniques known to the expert.

In connection with the impregnation of test layers with enzymes, proteins and especially bovine serum albumin have already been used as so-called protective proteins. They have been added in large amounts to the impregnation solution in order to stabilise the enzyme in the impregnation solution. However, a sufficient availability of the enzymes after prolonged storage cannot be achieved in this way.

It is important that the protein coating and the elutable reagent are applied in two separate steps. This does not mean that two layers exactly separated from one another are necessarily present on the solid component. On the contrary, it can be that, depending upon the microstructure of the solid component, a certain mixing up of the layer of insoluble protein and the layer of the biochemical reagent takes place. However, the effect according to the present invention does not take place when the protein and the reagent are mixed in a liquid state and then coated in one step on to the test layer or the corresponding component of the test layer.

DETAILED DESCRIPTION OF THE PREFERRED EMBODIMENTS

Figure 1:
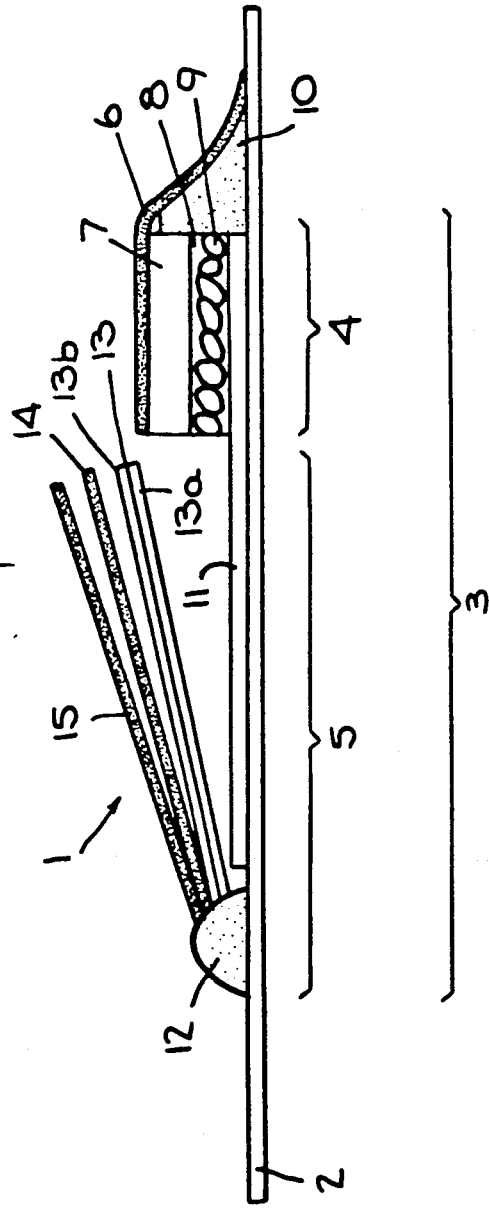
FIG. 1 is a side view of a test carrier according to the present invention.

The test carrier 1 illustrated in FIG. 1 has, in principal, the form of a test strip. However, it is a high quality analysis system which can hardly be compared with the previously known test strips, especially for carrying out immunological determinations.

On a base layer 2 is present a test 3 which extends only over a part of the length of the base layer 2. The test region 3 can be divided into a sample application zone 4 and an evaluation zone 5.

In the sample application zone 4, there can be seen, going from above downwardly, a covering mesh 6, an erythrocyte separation layer 7 and a reagent layer 8 which are fixed with a melt adhesive strip 10 to the base layer 2.

A liquid transport layer 11 of an absorbent material, which is also fixed with the melt adhesive strip 10, extends from the sample application zone 4 into the evaluation zone 5. Above the region of the liquid transport layer 11 not covered by the layers 7 to 9, there are present three layers which are fixed with a melt adhesive strip 12 onto the base layer 2 in such a way that, without external pressure, they project obliquely from the base layer 2 and do not touch it. These three layers are a test layer 13 with a carrier-fixed immunological reagent, a reagent layer 14 and a covering film 15.

The illustrated preferred test carrier is especially suitable for carrying out immunological determinations which are similar to the so-called IEMA principle. If, for example, an antigen (Ag) contained in a sample is to be determined, the analysis takes place in the following way:

A droplet of blood (about 30 μl.) is applied above the erythrocyte separation layer 7 to the covering mesh 6 and penetrates through the erythrocyte separation layer 7 which can be constructed, for example, in the manner described in U.S. Pat. No. 4,477,575; herein incorporated by reference. The serum thus obtained penetrates into the layer 8.

The layer 8 is a fabric 9 impregnated with a reagent. It contains an antibody (Ab) for the Ag which is labelled enzymatically and is present in excess with with regard to the maximum Ag concentration in the sample. This antibody-enzyme conjugate (AbE) is dissolved by the serum penetrating in, complexes thereby being formed between the AbE and the Ag, which are referred to as Ag-AbE. Since the AbE is present in excess, when equilibrium is reached, free conjugate AbE is left over after the reaction.

The purpose of the layer 13 is to separate this AbE, which would disturb the further detection, by an immunological binding of the Ag-AbE complexes. Therefore, it is also referred to as an immunolgoical separation layer. It contains the analyte or an analyteanalogous antigen in carrier-fixed form.

After the expiry of a predetermined incubation time, in which the equilibrium has adjusted in the preceding reaction, a pressure is exerted from above on the layer 13-15. This can take place manually or mechanically with the help of a part of an apparatus, for example in the manner described in European Patent Specification No. 0,129,220, to which U.S. Pat. No. 4,780,283 corresponds. Due to the pressing on, the immunological separation layer 13 comes into contact with the liquid transport layer 11 and the components contained therein pass into the layer 13, the noncomplexed AbE thereby coupling on to the fixed Ag. On the other hand, the Ag-AbE complexes can pass further on unhindered insofar as they are not held back by undesired non-specific binding.

The reagent layer 14 contains a colour-forming substrate for the labelling enzyme. When the liquid has reached the substrate, the enzyme of the free Ag-AbE complexes catalyses the colour reaction of the substrate. The rate of the colour change is, therefore, a measure for the free complexes Ag-AbE which have reached the reagent layer 14. This is, in turn, a measure for the Ag contained in the sample. With regard to the course of an IEMA test on a test carrier, reference is additionally made to Federal Republic of Gemary Patent Specification No. 36 38 654.

In the test carrier of FIG. 1, the protein coating according to the present invention is realised in the reagent layer 8 and in the immunological separation layer 13.

In the case of the layer 8, the reagent carrier function is dominant although the layer also causes a liquid transport from layer 7 to layer 11. The fabric 9 forms the solid component which is coated first with the insoluble protein and then with the reagent, in this case the soluble antibody-enzyme conjugate. In this way, a substantially complete elution of the reagent is achieved, even after a long period of storage.

In the case of the immunological separation layer 13, the transport function is of prime importance, although the layer also serves as reagent carrier for the carrier-fixed Ag. This layer is of special importance for the function of the test carrier because the colour change in the substrate layer 14 is only a reproducible measure for the Ag concentration when the layer 13 provides for a complete separation of the non-complexed AbE and, at the same time, allows the Ag-AbE complexes to pass through completely or at least in a uniform amount.

Figure 2:
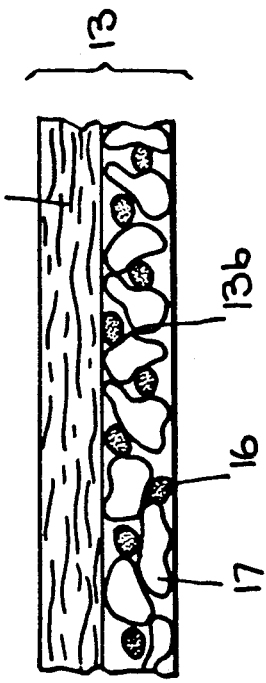
FIG. 2 is a cross-sectional view through a test layer with a particle-composite structure.

The principle construction of a preferred separation layer 13 is illustration schematically in FIG. 2. It comprises a carrying fabric or fleece 13a and a coating applied thereon in the form of a particle composite structure 13b.

The particle composite structure 13b contains reagent carrier particles 16 which, in the described example, carry the carrier-fixed antigen. Furthermore, it contains opener particles 17. The particles 16 and 17 form two solid components of the layer 13b. They are bound by an appropriate adhesive, which for the sake of clarity is not illustrated in the Figure, to give a three-dimensional, open-pored, layered structure.

The layer 13b is preferably produced by direct coating on to the carrying fabric of fleece 13a. The coating mass is a solution or dispersion of film-forming organic synthetic resin which contains the particles 16 and 17. The viscosity of the coating mass is so adjusted that, on the one hand, it penetrates into the fabric but, on the other hand, remains preponderantly on one side of the fabric. In this regard, reference is made to U.S. Pat. No. 4,604,264.

A separation layer constructed on these principles has proved to be very effective with regard to the separation of AbE but we have found the untreated opener particles 17 cause non-specific binding and thereby hold back the Ag-AbE complexes in a poorly reproducible manner so that the measurement results can be considerably falsified.

This non-specific binding can be overcome by coating the opener particles, before incorporation into the particle composite structure, with an insoluble protein. The opener particles preferably consist of an inorganic material based on silicon dioxide and especially of diatomaceous earth, which in the following is also referred to as Celatom. Supplymentary hereto, reference is made to U.S. Pat. No. 4,312,834.

In general, such a test layer construction proves to be especially advantageous in those cases in which, during the course of the test, a liquid which contains a macromolecular organic test component flows through the test layer as unhindered as possible. Undesired binding of this test component to solid components of the test layer can, in this case, be prevented by protein coating of the appropriate components.

In the case of a test construction of the here-described kind for the determination of T4, practical results have shown that the coating of the separation layer leads to a substantially improved differentiation of the colour formation. Thus, for example, in the case of a graduation of the T4 concentration in the clinically relevant range of from 0.55 to 20.9 $\mu$g./dl. T4, with a separation layer with casein-treated Celatom, there was measured a change of the diffuse reflectivity of more than 20%. With untreated Celatom, on the other hand, there was only obtained a change of about 4.5% reflectivity which does not permit a quantitative evaluation.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

EXAMPLE 1

Demonstration of the improved availability of a biochemical reagent by casein pretreatment in comparison with the prior art.

CASEIN PRETREATMENT 300 cm$^2$ of a multifilar polyester fabric (2F77), Schweizer Seidengazefabrik Thal, Switzerland) are treated for 30 minutes with the following solution: 0.1% casein and 0.1% Triton $\times$100 in water, adjusted to pH 11.5 with a 1N aqueous solution of sodium hydroxide. Subsequently, the fabric is washed neutral with 0.15M sodium phosphate buffer (pH 7.0) and dried for 30 minutes at 50° C.

On to this casein-pretreated fabric, as well as on to an untreated fabric, there is impregnated an antitheophylline-IgG-$\beta$-galactosidase conjugate with the following variants and, in each case, dried for 1 hour at 40° C.

a) The conjugate is adjusted in PBS (phosphate-buffered saline containing 0.15M sodium chloride and 0.01M sodium phosphate; pH 7.4) containing 0.1% Triton $\times$100 to 50 U/ml. enzyme activity and impregnated on to the untreated fabric.

b) The conjugate is adjusted in PBS containing 0.1% Triton $\times$100, 5 mg./ml. bovine serum albumin and 2% trehalose to 50 U/ml. enzyme activity and impregnated on to the untreated fabric.

c) The conjugate is adjusted in PBS containing 0.1% Triton $\times$100 to 50 U/ml. enzyme activity and impregnated on to the casein-pretreated fabric.

d) The conjugate is adjusted in PBS containing 0.1% Triton $\times$100, 5 mg./ml. bovine serum albumin and 2% trehalose to 50 U/ml. enzyme activity and impregnated on to the casein-pretreated fabric.

The pieces of fabric a) to d) are stored in aluminium tubes with a drying agent for up to 6 weeks at different temperatures (4° C., 25° C. and 45° C.), the still present enzyme activity being investigated at different times.

COMPARATIVE DETERMINATION OF THE ENZYME ACTIVITY $6\times 6$ mm. sized pieces of fabric are eluted with 100 $\mu$l. PBS for 20 seconds with shaking.

In microtitre plates, 50 $\mu$l. of the eluate are added to 200 $\mu$l. of substrate solution (1 mM chlorophenol red galactoside in 25 mM aqueous sodium chloride solution, 5 mM magnesium chloride, 20 mM HEPES, pH adjusted to 7.2 with sodium hydroxide solution).

The extinctions are measured at different times and recalculated into mE/min.

The results of the temperature stressing investigation are set out in the following Table 1:

TABLE 1

| variants | stressing time (weeks) | unit: mE/10 min. | | |
| --- | --- | --- | --- | --- |
| | | 4° C. | 25° C. | 45° C. |
| a) without addition | 0 | 698 | 698 | 698 |
| | 2 | 682 | 672 | 569 |
| | 4 | 670 | 621 | 431 |
| | 6 | 559 | 428 | 173 |
| b) trehalose albumin | 0 | 705 | 705 | 705 |
| | 2 | 697 | 670 | 653 |
| | 4 | 675 | 635 | 551 |
| | 6 | 598 | 544 | 361 |
| c) casein | 0 | 710 | 710 | 710 |
| | 2 | 693 | 730 | 680 |
| | 4 | 711 | 729 | 730 |
| | 6 | 697 | 695 | 705 |
| d) casein trehalose albumin | 0 | 720 | 720 | 720 |
| | 2 | 722 | 740 | 708 |
| | 4 | 698 | 732 | 719 |
| | 6 | 703 | 735 | 726 |

It can be seen that the availability of the conjugate after the temperature stressing is, in the case of the casein-coated variants, almost complete, whereas in the case of the variants not coated with casein, it is very considerably reduced by the stressing.

According to the present invention, in the case of a storage stability of 6 weeks at 45° C., as is given in variants c) and d) according to the present invention, a storage stability of at least 2 years at ambient temperature is to be expected.

The given measurement values are average values from, in each case, 6 individual values. It is a laboratory pattern with a comparatively large variation (vK 5-10%).

EXAMPLE 2

Availability-increasing action of the casein pretreatment on pure β-galactosidase, as well as on various β-galactosidase conjugates.

600 cm$^2$ of a polyester fleece (DuPont, Reemay 2033) are, as in Example 1, coated with casein and dried.

In each case, a quarter of this fleece is impregnated with the following samples:

a) a high molecular weight (mole weight greater than 10 million) anti-theophylline-IgG-β-galactosidase conjugate;

b) a low molecular weight (mole weight less than 2.5 million) anti-theophylline-Fab-β-galactosidase conjugate;

c) a tetraiodothyronine-β-galactosidase conjugate (as an example of a hapten-β-galactosidase conjugate);

d) unmodified β-galactosidase.

In each case, solutions are prepared with 50 U/ml. enzyme activity, 0.1% Triton ×100, 5 mg./ml. bovine serum albumin and 2% trehalose in PBS and used for impregnation of the samples which are then dried for 1 hour at 40° C.

The pieces of fabric are then stored in aluminium tubes with a drying agent for 6 weeks at 45° C.

Thereafter, the still present enzyme activity is determined (average values of 6 individual values, vK about 8%), the results obtained being set out in the following Table 2:

TABLE 2

|  | mE 10/min. | | |
| --- | --- | --- | --- |
|  | initial activity | activity after 6 weeks at 45° C. | % residual activity |
| HM-IgG conjugate | 636 | 634 | 99 |
| NM-Fab conjugate | 610 | 622 | 100 |
| T$_4$-Gal conjugate | 574 | 554 | 96 |
| β-galactosidase | 600 | 619 | 100 |

EXAMPLE 3

Avoidance of non-specific bindings by coating of Celatom with casein.

a) Casein loading

A 0.5% casein suspension (Serva, Heidelberg, Federal Republic of Germany) in distilled water is adjusted to pH 12 with 2M aqueous sodium hydroxide solution and 0.5 g. of Celatom is introduced into 3.5 ml. of this solution. After stirring for 30 minutes, the suspension is readjusted to pH 5 with hydrochloric acid, the casein thereby precipitating out. It is filtered off with suction over a G3 frit (16–40 μm. pore size) and washed neutral with PBS. It is either dried at 45° C. or lyophilised.

b) Non-specific binding of (T4)-Gal conjugate on to unloaded Celatom and on to Celatom loaded with casein In each case, 100 μl. (T4)-Gal conjugate (10 IU/ml.) are mixed with 100 μl. of a 20% Celatom suspension in PBS, the Celatom used being that produced according to a) and untreated. After incubation for 5 minutes at ambient temperature, it is centrifuged off, the supernatant is taken and the enzyme activity determined in E/min. in the supernatant. As control,.instead of the Celatom suspension, there is used 100 μl. PBS.

The results obtained are set out in the following Table 3:

TABLE 3

|  | control | unloaded Celatom | caseinated Celatom |
| --- | --- | --- | --- |
| Δ E/min. | 1.246 | 0.024 | 1.227 |
| % activity in the supernatant | 100 | 1.9 | 98.5 |
| % non-specific binding | — | 98.1 | 1.5 |

We claim:

1. A layered test carrier device for analysis of an analyte in a liquid sample, comprising:
   (a) a porous test layer having a 3-dimensional open pored structure and comprising a solid component coated with a protein which is insoluble under conditions of use and which also prevents undesired binding of a macromolecular substance which (i) might be present in the liquid sample and is to be determined or (ii) is present in said device and reacts with the analyte to be determined, and
   (b) a reagent incorporated into said device which reacts with said analyte to produce a detectable signal representative of said analysis, said reagent positioned at a point in said device contacted by said liquid sample after said liquid sample contacts said porous test layer.

2. Layered test carrier device of claim 1, wherein said protein is casein.

3. Layered test carrier device of claim 1, wherein said reagent comprises a biochemical substance which is contained in said porous test layer in elutable form.

4. Layered test carrier device of claim 1, wherein said reagent comprises an enzyme.

5. Layered test carrier device of claim 4, wherein said enzyme is galactosidase.

6. Layered test carrier device of claim 1, wherein said reagent is a galactosidase conjugate.

7. Layered test carrier device of claim 1, wherein said porous test layer contains a textile structure.

8. Layered test carrier device of claim 1, wherein said porous test layer comprises polyester or polyamide.

9. Layered test carrier device of claim 1, wherein said solid component comprises particles.

10. Layered test carrier device of claim 9, wherein said particles consist of inorganic material.

11. Layered test carrier device of claim 10, wherein said inorganic material is silicon dioxide.

12. Method for determining an analyte in a liquid sample comprising contacting said liquid sample to the layered test carrier device of claim 1 and evaluating reaction between said analyte and said reagents as an indication of said analyte.

13. Method for determining an analyte in a liquid sample comprising contacting said liquid sample to the layered test carrier device of claim 2 and evaluating reaction between said analyte and said reagents as an indication of said analyte.

14. Method for determining an analyte in a liquid sample comprising contacting said liquid sample to the layered test carrier device of claim 3 and evaluating reaction between said analyte and said reagents as an indication of said analyte.

15. Method of claim 14, wherein said biochemical substance comprises an enzyme.

16. Method of claim 14, wherein said biochemical substance is a conjugate of an immunoreactant and an enzyme.

17. Method of claim 15, wherein said enzyme is galactosidase.

18. Method of claim 16, wherein said enzyme is galactosidase.

19. Method for determining an analyte in a liquid sample comprising contacting said liquid sample to the layered test carrier device of claim 1, under conditions permitting flow of said liquid sample containing said analyte and said macromolecular test substances through said porous test layer and said evaluating reaction between said analyte and said reagents as an indication of said analyte.

* * * * *

UNITED STATES PATENT AND TRADEMARK OFFICE
CERTIFICATE OF CORRECTION

PATENT NO. : 5,132,208

DATED : July 21, 1992

INVENTOR(S) : Helmut Freitag et al.

It is certified that error appears in the above-identified patent and that said Letters Patent is hereby corrected as shown below:

Column 1, line 53: change "fulfil" to -- fulfill --.

Column 2, line 18: change "Different" to -- different --.

Column 3, line 36: change "as" to -- an --.

Column 5, line 24: after "test" insert -- region --.

Signed and Sealed this

Twenty-fifth Day of January, 1994

Attest:

BRUCE LEHMAN

*Attesting Officer*  *Commissioner of Patents and Trademarks*